United States Patent [19]
Walsh

[11] Patent Number: 6,139,872
[45] Date of Patent: Oct. 31, 2000

[54] METHOD OF PRODUCING A VITAMIN PRODUCT

[75] Inventor: Leo Walsh, Lisle, Ill.

[73] Assignee: Henkel Corporation, Gulph Mills, Pa.

[21] Appl. No.: 08/917,049

[22] Filed: Aug. 13, 1997

Related U.S. Application Data

[63] Continuation-in-part of application No. 08/696,767, Aug. 14, 1996, Pat. No. 5,686,632.

[51] Int. Cl.[7] .............................. A61K 9/14; A61K 9/20
[52] U.S. Cl. ..................... 424/464; 424/465; 424/489; 424/195.1; 514/951
[58] Field of Search .................................. 424/464, 465, 424/489, 195.1

[56] References Cited

U.S. PATENT DOCUMENTS

| | | | |
|---|---|---|---|
| 2,680,749 | 12/1954 | Cawley et al. | 260/345.5 |
| 3,538,119 | 11/1970 | Grant | 260/345.5 |
| 3,551,457 | 12/1970 | Ross | 260/345.5 |
| 3,655,852 | 4/1972 | Koff et al. | 264/115 |
| 3,864,469 | 2/1975 | Reiser et al. | 424/22 |
| 3,962,416 | 6/1976 | Katzen | 424/19 |
| 4,232,047 | 11/1980 | Sair et al. | 426/96 |
| 4,752,496 | 6/1988 | Fellows et al. | 427/27 |
| 4,861,580 | 8/1989 | Janoff et al. | 424/1.1 |
| 4,869,966 | 9/1989 | Samuelson et al. | 428/428 |
| 4,870,196 | 9/1989 | Thorengaard | 549/410 |
| 4,875,847 | 10/1989 | Wenger et al. | 425/204 |
| 4,880,018 | 11/1989 | Graves, Jr. et al. | 131/375 |
| 4,925,667 | 5/1990 | Fellows et al. | 424/401 |
| 4,936,074 | 6/1990 | Graham | 53/440 |
| 4,981,711 | 1/1991 | Kearns et al. | 426/1 |
| 4,999,208 | 3/1991 | Lengerich et al. | 426/549 |
| 5,041,278 | 8/1991 | Janoff et al. | 424/1.1 |
| 5,126,328 | 6/1992 | Bower et al. | 514/21 |
| 5,132,133 | 7/1992 | Huber et al. | 426/241 |
| 5,148,821 | 9/1992 | Best et al. | 131/370 |
| 5,153,177 | 10/1992 | Chaundy et al. | 514/21 |
| 5,232,712 | 8/1993 | Mills et al. | 425/133.1 |
| 5,234,634 | 8/1993 | Janoff et al. | 264/4.1 |
| 5,262,190 | 11/1993 | Cunningham et al. | 426/549 |
| 5,330,689 | 7/1994 | Janoff et al. | 264/4.3 |
| 5,334,407 | 8/1994 | Donnelly et al. | 426/618 |
| 5,397,587 | 3/1995 | Thompson et al. | 426/557 |
| 5,407,661 | 4/1995 | Simone et al. | 426/807 |
| 5,418,010 | 5/1995 | Janda et al. | 427/213.31 |
| 5,418,154 | 5/1995 | Aebischer et al. | 435/182 |
| 5,427,809 | 6/1995 | Donnely et al. | 426/448 |
| 5,429,835 | 7/1995 | Wenger et al. | 426/557 |
| 5,456,923 | 10/1995 | Nakamichi et al. | 424/489 |
| 5,501,868 | 3/1996 | Collings et al. | 426/623 |
| 5,549,917 | 8/1996 | Cherukuri et al. | 426/96 |
| 5,603,971 | 2/1997 | Porzio et al. | 426/96 |
| 5,686,632 | 11/1997 | Walsh | 549/410 |
| 5,785,944 | 7/1998 | Miller | 423/700 |

FOREIGN PATENT DOCUMENTS

| | | |
|---|---|---|
| 0369445 | 5/1990 | European Pat. Off. . |
| 0580860 | 4/1992 | European Pat. Off. . |
| 866489 | 12/1959 | United Kingdom . |
| 1007161 | 10/1965 | United Kingdom . |
| 1114150 | 2/1967 | United Kingdom . |
| 8503414 | 9/1985 | WIPO . |
| 8702219 | 4/1987 | WIPO . |
| 9205708 | 4/1992 | WIPO . |
| 9218106 | 10/1992 | WIPO . |
| 9403158 | 2/1994 | WIPO . |
| 9423593 | 10/1994 | WIPO . |
| 9522319 | 9/1995 | WIPO . |
| 9629061 | 9/1996 | WIPO . |

OTHER PUBLICATIONS

*Encyclopedia of Polymer Science & Engineering*, vol. 11, pp. 262–267, (J. Wiley & Sons, Inc., NY, NY 1988).
C.E. Capes, "Size Enlargement," *Encyclopedia of Chemical Technology*, vol 21, pp. 77–105, (Kirk–Othmer, eds., John Wiley and Sons, Inc., NY, NY 1983).
Handbook of Chemistry & Physics, p. F–158 (57th ed., CRC Press, Cleveland, Ohio, 1976).
"Prema Mill, Model SM–18", New Product Data, Prater Industries, Inc., 1997.
"Wenger Mag Series Twin Screw Extruder Systems", Physical Information, Wenger, Jan. 1995.
"Size Reduction", Kirk–Othmer Encyclopedia of Chemical Technology, vol. 21 pp. 132–162, Jan. 1983.

*Primary Examiner*—James M. Spear
*Attorney, Agent, or Firm*—John E. Drach; Martin G. Meder; Daniel S. Ortiz

[57] ABSTRACT

A process for producing a nutrient supplement powder is provided. The process forms a powder into a plastic mass which is not completely molten. The plastic mass is then formed into an elongated shape and allowed to cool to set to a solid state. The solid is then comminuted to obtain a powder having a desirable particle size, e.g. not more than 5% by weight through a 120-mesh sieve and not more than 5% by weight retained on a 14-mesh sieve.

41 Claims, No Drawings

METHOD OF PRODUCING A VITAMIN PRODUCT

RELATED APPLICATIONS

This application is a continuation-in-part of U.S. application Ser. No. 08/696,767, filed Aug. 14, 1996 U.S. Pat. No. 5,686,632, the contents of which are incorporated herein by reference.

FIELD OF THE INVENTION

The present invention relates to a method of producing a particulate material tablet from heat sensitive nutritional supplement materials. The particulate materials have a desirable particle size.

BACKGROUND OF THE INVENTION

Nutritional supplements such as tocopherol compounds, also designated as vitamin E, are active components in vegetable oils. Vitamin E activity refers to the physiological activity of this group of nutritional materials. Materials having a vitamin E activity all belong to a distinct series of compounds which are all derivatives of chroman-6-ol. These compounds are all tocol derivatives having an isoprenoid C16-sidechain. The term "tocol" is used to mean 2-methyl-2-(4',8',12'-trimethyltridecyl)chroman-6-ol. These compounds are alpha-, beta-, gamma-, and delta-tocopherol, and are of primary importance for vitamin E activity. Of these, alpha-tocopherol has the highest vitamin E activity and is the most valuable. The invention also relates to other nutrient supplements, such as phytosterols vitamins, which have relatively low melting points and are difficult to form into particulate materials.

The naturally occurring tocopherol homologs are generally isolated from natural products such as vegetable oil sources by various combinations of procedures such as esterification, saponification, extraction, distillation, ion exchange, adsorption chromatography, precipitation of sterols, and crystallization. The tocol concentrate isolated will vary depending on the particular separation technique used in addition to the vegetable source. One such concentrate, for example, contains mixtures of tocopherol with approximately 40% by weight residual sterols and hydrocarbons.

A well known commercial activity is the conversion of tocopherol, and especially d-alpha-tocopherol, into a solid form for convenient human consumption. One of the best methods commercially used to solidify tocopherol is to prepare tocopheryl succinate. Typically, tocopheryl succinate is prepared by reacting tocopherol with succinic anhydride, and then isolating the half ester product by crystallization. References describing methods of this nature are described in U.S. Pat. No. 3,538,119 and in British Patent No. 866,489. Another reference which describes both the preparation of alpha-tocopheryl succinate and its recovery is British Patent No. 1,114,150.

For medicinal and health applications requiring tocopherol, solid tocopherol derivatives are preferred. It is desired that such tocopherol derivatives be capable of dissolving in an aqueous solution and be highly potent with a high degree of vitamin E biological activity per unit. The preparation of tocopherol derivatives is described in U.S. Pat. No. 2,680,749, which describes, as a preferred method, reacting tocopherol with a suitable polybasic acid anhydride such as succinic acid anhydride under usual esterification conditions.

Tocopheryl succinate, which is a vitamin E, melts at about 73°–78° C. It is a white solid material which at room temperature is waxy and tacky and which has poor flow properties. Furthermore, the commercially available tocopheryl succinate ordinarily has a broad particle size distribution with many fine particles which causes the powder to be cohesive and to form lumps.

A number of attempts have been made to prepare free-flowing tocopheryl succinate with and without additives. A prior art method is disclosed in U.S. Pat. No. 3,551,457. In this method tocopheryl succinate is heated to melt it, i.e., to about 85° C., and the melt is poured into a shallow pan so as to form a layer having a thickness of between 0.3 and 2.5 cm, after which the melt is allowed to harden and crystallize over a period of 12–24 hours. The resulting mass is then ground at a low temperature, preferably at a temperature of about −80° C.

British Patent No. 1,007,161 discloses another method of preparing free-flowing, powdered tocopheryl succinate having a high bulk density. In the method tocopheryl succinate is melted and the melt is dispersed in an aqueous solution containing a thickening agent in the form of methyl cellulose, and subsequently the dispersion formed is quickly cooled so as to cause the tocopheryl succinate to crystallize to form fine particles which are separated and dried. A product thus prepared has a relatively broad particle size distribution which causes problems in the treatment of the product in known tabletting machines. Furthermore, the use of methyl cellulose as thickening agent results in a certain tackiness which imparts to the product a tendency to, adhere to e.g., parts of the tabletting machine.

U.S. Pat. No. 4,870,196 (Thorengaard) discloses a method of preparing powdered, free-flowing tocopheryl succinate having a high bulk density comprising melting a mixture of tocopheryl succinate and wax, spraying the melt in a spraying zone containing a cloud of a powdering agent consisting of fine tocopheryl succinate and an additional powdering agent, and maintaining the product formed in a fluidized state by introducing cooling air until the tocopheryl succinate particles have hardened, and separating the product formed into a product fraction and a fine fraction, and recycling the fine fraction to the spraying zone.

Thorengaard reports that attempts to prepare tocopheryl succinate in the form of particles coated with other agents that the ones described above have not produced satisfactory results as these attempts have resulted in the reduction of the tocopheryl succinate content of the final product. It is stated that this is undesirable because of the subsequent preparation of high-dosed capsules and tablets since for such use it is desirable that the starting material contains as much tocopheryl succinate as possible and that it also has a high bulk density.

Phytosterols may be used in the present invention and are also derived from the plant kingdom, and some of them are desirable nutritional supplements because they are believed to reduce cholesterol.

SUMMARY OF THE INVENTION

This invention relates to a method of producing a particulate nutritional supplement comprising heating a mass of the nutritional supplement to an elevated temperature to form a plastic mass and cooling said plastic mass to form a solid. The elevated temperature is low enough that a plastic mass is formed but the nutritional supplement composition is not completely melted. Thus, the temperature of the entire mass will not exceed the melting point of the nutritional supplement. The mass is typically divided into discrete portions, e.g. multiple ropes of extrudate, prior to cooling and setting. The extruder may be fit with an injection molding head to form tablets directly or with an atomizer head to form particulates. The mass is preferably essentially free of added physiologically inert binders, e.g. natural or synthetic polymers that are added thereto. The material can comprise mixtures of materials, the nutritional supplement acting as a nutritionally active matrix for other nutritional supplements (vitamins minerals and the like) not capable of behaving plastically, and thus less desirable as a nutritionally active matrix. The preferred active matrix nutritional supplements are tocopheryl succinate and phytosterols. Unexpectedly, these materials are believed to exhibit plastic behavior upon heating and are defined as "plastic nutritional supplements" to avoid the awkward "nutritional supplements that are capable of becoming plastic upon heating."

Generally the method is useful for providing particulate materials from relatively low melting point materials which are slow to crystalize. The mixture is mixed and heated to form a plastic mass. The plastic mass is preferably extruded and cooled, then ground to form the particulate material. All quantities herein, except in the examples, are understood to be modified by "about."

DETAILED DESCRIPTION OF THE INVENTION

This invention relates to a method for producing particulate materials. The starting material is a solid material and at no point in this process of size enlargement is the mass of material heated above its melting point so as to melt the entire mass of material. Thus, the plastic mass of material is a shapeable, e.g. moldable or extrudable, material as opposed to a fully liquid melt. The product of the process is, in a sense, agglomerated particles of the nutritional supplement material and the process may be characterized as an agglomeration process. The nutritional supplement materials which can be processed by the method of the invention comprise materials which are solid at 40° C. and are molten by 170° C. Preferably, materials which are solid at 45° C. and are molten at 100–125° C. and most preferably materials that are solid at 50° C. and are molten at 90° C., when using tocophry succinate.

Examples of the above include organic materials such as tocopheryl succinate and phytosterols and their derivatives such as sterols, stanols (hydrogenated sterols), sterol esters and stanol esters. Specific examples of these phytosterols and their melting points include: alpha-sitosterol (164–166° C.), beta-sitosterol (140° C.), gamma-sitosterol (no data), campesterol (157–158° C.), stigmasterol (170° C.), stigmastanol (144–145° C.), brassicasterol (151–152° C.) and ergostanol (144–145° C.). Blends of phyto sterols based on plant extracts that melt between 135–141° C. are 43–53 wt. % beta-sitosterol, 22–26 wt. % campesterol, 17–19 wt. % stigmasterol, less than 2 wt. % stigmastanol (a.k.a. beta-sitostanol), less than 2 wt. % campestanol, 2 wt. % brassicasterol. At least 80 wt. % active sterol and stanol in the plant extract is desired, the balance being tocopherol, squalene and other plant wax impurities.

To the above active matrices may be added nutritional supplements with less plastic behavior as solid state solutions or insoluble particulate filler and oils.

These nutritional supplement additives of lesser plasticity include vitamins such as: vitamin A (retinol, retinyl palmitate and retinol acetate), vitamin B1 (thiamin, thiamin hydrochloride and thiamin mononitrate), vitamin B2 (riboflavin), vitamin B3 (niacin, nicotinic acid and niacinamide) vitamin B5 (pantothenic acid, calcium pantothenate, d-panthenol and d-calcium pantothenate), vitamin B6 (pyridoxine, pyridoxal, pyridoxamine and pyridoxine hydrochloride), vitamin B12 (cobalamin and cyanocobalamin), folic acid, folate, folacin, vitamin H (biotin), vitamin C (ascorbic acid, sodium ascorbate and calcium ascorbate), vitamin D (cholecalciferol, calciferol and ergocalciferol), vitamin E (d-alpha-tocopherol, d-beta-tocopherol, d-gamma-ocopherol, d-delta-tocopherol and d-alpha-tocopheryl acetate) and vitamin K (phylloquinone and phytonadione).

Nutritional supplement additives also include minerals such as boron (sodium tetraborate decahydrate), calcium (calcium carbonate, calcium caseinate, calcium citrate, calcium gluconate, calcium lactate, calcium phosphate, dibasic calcium phosphate and tribasic calcium phosphate), chromium (gtf chromium from yeast, chromium acetate, chromium chloride, chromium trichloride and chromium picolinate) copper (copper gluconate and copper sulfate), fluorine (fluoride and calcium fluoride), iodine (potassium iodide), iron (ferrous fumarate, ferrous gluconate and ferrous sulfate), magnesium (magnesium carbonate, magnesium gluconate, magnesium hydroxide and magnesium oxide), manganese (manganese gluconate and manganese sulfate), molybdenum (sodium molybdate), phosphorus (dibasic calcium phosphate, sodium phosphate), potassium (potassium aspartate, potassium citrate, potassium chloride and potassium gluconate), selenium (sodium selenite and selenium from yeast), silicon (sodium metasilicate), sodium (sodium chloride), strontium, vanadium (vanadium sulfate) and zinc (zinc acetate, zinc citrate, zinc gluconate and zinc sulfate).

Nutritional supplement additives also include amino acids such as: alanine, arginine, asparagine, aspartic acid, carnitine, citrulline, cysteine, cystine, dimethyglycine, gamma-aminobutyric acid, glutamic acid, glutamine, glutathione, glycine, histidine, isoleucine, leucine, lysine, methionine, ornithine, phenylalanine, proline, serine, taurine, threonine, tryptophan, tyrosine and valine.

Nutritional supplement additives also include animal extracts such as: cod liver oil, marine lipids, shark cartilage, oyster shell, bee pollen and d-glucosamine sulfate.

Nutritional supplement additives also include unsaturated free fatty acids such as: linoleic, arachidonic and linolenic.

Nutritional supplement additives also include herbs and plant extracts such as: kelp, pectin, Spirulina, fiber, lecithin, wheat germ oil, safflower seed oil, flax seed, evening primrose, borage oil, black currant, pumpkin seed oil, grape extract, grape seed extract, bark extract, pine bark extract, french maritime pine bark extract, muira puama extract, fennel seed extract, dong quai extract, chaste tree berry extract, alfalfa, saw palmetto berry extract, green tea extracts, angelica, catnip, cayenne, comfrey, garlic, ginger, ginseng, goldenseal, juniper berries, licorice, olive oil, parsley, peppermint, valerian, white willow, yellow dock and yerba mate.

Nutritional supplement additives also include enzymes such as: amylase, protease, lipase and papain as well as miscellaneous substances such as: menaquinone, choline (choline bitartrate), inositol, carotenoids (beta-carotene, alpha-carotene, zeaxanthin, cryptoxanthin and lutein), para-aminobenzoic acid, betaine HCL, eicosapentaenoic acid, omega-3 fatty acids, alpha-lipoic acid, thiotic acid, 1,2-dithiolane-3-pentanoic acid, 1,2-dithiolane-3-valeric acid, flavanoids, flavanones, flavones, flavonols, isoflavones, proanthocyanidins, oligomeric proanthocyanidins, vitamin A aldehyde, a mixture of the components of vitamin $A_2$, the D Vitamins ($D_1$, $D_2$, $D_3$ and $D_4$) which can be treated as a mixture, ascorbyl palmitate and vitamin $K_2$.

Some vitamins such as trans vitamin $A_2$, 9, 13 di-cis vitamin $A_2$, and d-alpha tocopherol are liquids at room temperature. However, they can be treated by the method of the invention if they are heated in a mixture with other vitamins having melting points within the required range as long as the mixture can be solidified at room temperature. The method of the invention can be utilized to form particulate materials from vitamins which have melting points above 170° C. if they are mixed with the plastic nutrient supplements, tocopheryl succinate and phytosterols, having melting points within a 40° C. to 170° C. range.

The method of the invention is particularly useful for providing mixtures of vitamins in particulate form which can be easily tabletted or used to fill capsules.

Vitamins which are liquid at room temperature such as vitamin E (α-tocopherol), vitamin K, or vitamin E acetate can be mixed with the plastic nutrient supplements and formed as particulate materials by the method of the invention.

Nutritional supplements with melting points higher than 170° C. can be mixed with plastic nutritional supplements. When the nutritional supplements have a melting point far above 170° C., the particles of any additional supplements are supported in a matrix of the lower melting plastic supplements. The mixture can also contain vitamins which are liquid at room temperature as long as the mixture (high melting point vitamins, vitamins which are molten at temperatures from 40° C. to 170° C., and liquid vitamins) is a solid at room temperature.

The process will be described in relation to the vitamin tocopherol succinate but it is realized that the method can be applied to phytosterols as well and mixtures of plastic and less plastic nutritional supplements. The present invention permits the manufacture of multiple vitamin formulations in particulate form which can be easily fed to machines for automatically forming tablets and filling capsules. Also, the extruder can be fitted with an injection molding head comprising a die with runners and tablet shaped cavities to form tablets or pills directly or fitted with an atomizer head to form particulates.

The materials which can be processed by the method of the invention include single nutritional supplements and mixtures of supplements in variable proportions. The proportions are dependent upon the physical properties of the materials in the mixture and in particular their melting points. Generally liquid supplements can only be mixed in small portions with materials which are liquid in themselves at 40° C. or 50° C. High melting point materials (melting point above 170° C.) can be mixed with lower melting point materials in higher amounts as long as the product has sufficient strength to be comminuted without crumbling or producing unacceptable amounts of fine particles.

The invention will be described in relation to the preparation of powder tocopherol succinate but the method can be applied to other plastic nutritional supplements which melt in the range of 40° C. to 170° C. alone, in admixture with each other or in admixture with vitamins which are liquid at temperatures below 40° C.

The vitamin materials which have melting points from 40° C. to 170° C. can be difficult to prepare in a particulate form on a commercial scale due to the difficulty with solidifying some of the compositions if they are melted. The present method does not form a melt of the material but only heats the material to a temperature at which a plastic mass which can be extruded is formed. Formation of a plastic mass permits rapid solidification of the material after the material is forced from the extruder.

The temperature of the material in the extruder is below the melting point of the plastic nutritional supplements but at a temperature at which a plastic mass is formed. Generally the temperature of the plastic mass in the extruder will be from 2° C. to 25° C. and preferably at least 5° C. below the melting point of the plastic supplements which melt within the range of 40° C. to 170° C. The temperature is controlled at the point where the mass in the extruder is plastic not molten. The products of the invention are substantially free of nutritionally inactive binders for the plastic nutrient supplement which forms the particulate material. While not wishing to be held to any theory, it is possible for a material to be at its melting temperature but yet not completely liquified.

The invention will be described in relation to forming a power from the partial succinic acid ester of a tocopherol (hereinafter tocopherol succinate); however, the method can be applied to form particulate material from the plastic nutritional supplements, mixtures and other compositions herebefore described.

In typical embodiments, the process can be characterized as extrusion of a plastic mass of particulate tocopheryl succinate (preferably the starting material comprises a substantial portion, e.g. at least 5% by weight, of particles which pass through an 80-mesh (U.S. standard) sieve) wherein the temperature of the particulate material is sufficient to plastify the mass, but insufficient to melt all of the solid particles of said tocopheryl succinate. The tocopheryl succinate to be used in the practice of the invention is typically in the free acid form. However, pharmaceutically acceptable salts, e.g. the sodium or potassium salts may also be useful.

The tocopheryl succinate or other plastic nutritional supplement used as a starting material in this invention are, typically, initially in the form of particulate material which can be mixed with other vitamins some of which may be liquid.

The tocopheryl succinate is preferably free of added inactive binders. Examples of binders include water-soluble celluloses, pregelatinized starches, and water-soluble macromolecules. The water-soluble celluloses include hydroxypropylcellulose, hydroxymethylcellulose, hydroxypropylmethylcellulose, carboxymethylcellulose and methylcellulose. A pregelatinized starch is a product obtained, for example, by heating a dispersion of starch in water, followed, as desired, by drying. Examples of water-soluble macromolecules includes polyvinylpyrrolidone (e.g. M.W. 10,000–100,000), polyvinyl alcohol (e.g. M.W. 10,000–50,000), dextrin, gum arabic, gum acacia, and gelatin. The tocopheryl succinate is also typically essentially free of solvents such as water or organic solvents, e.g. alcohols (e.g. methyl alcohol, ethyl alcohol, isopropyl alcohol) and ketones (e.g. acetone) and hydrocarbons, (e.g. hexane).

The tocopheryl succinate particulate material is subjected to sufficient heat and pressure to render it plastic. However, the temperature must be low enough that the entire mass does not melt. Without wishing to be bound by any particular theory, unless otherwise expressly noted, it is believed that the predominant portion by weight of the mass remains as solid particles, but that these particles are mixed with a phase of the tocopheryl succinate that is rendered fluid as a result of the heat and/or pressure. Upon exit of the resulting plastic mass from the zone of heat and/or pressure, the fluid phase reverts to solid form much more quickly than a fully melted liquid of tocopheryl succinate.

An extruder has been found to be particularly useful in forming and shaping the plastic mass of tocopheryl succinate. Extruders are generally described in *Encyclopedia of*

*Polymer Science and Engineering,* vol. 11, pp. 262–267 (John Wiley & Sons, Inc., N.Y., N.Y. 1988) the disclosure of which is incorporated herein by reference. The extruders useful herein may vary. Although single screw extruders can be employed, preferred extruders are the twin screw extruders of which the co-rotating twin screw extruders are especially preferred. Of particular interest are the so-called "cooker extruders" which provide for heating of the materials which are introduced within the extruder. Various screw configurations can be employed. For example, screws having combinations of elements for feeding, mixing, pumping, shearing, and the like, can be selected as desired for optimum results. Screws having sections or elements which provide relatively large output capacities, which have interrupted or nonconjugated flights, or which are "counter-flighted" or "reversing" also can be employed. Typical screw elements as well as screws having combinations of such elements are available from extruder manufacturers. The length to diameter ratio of the extruder will typically range from 10:1 to 50:1. The plastic mass is preferably divided into discrete portions, typically by passage through a die having a plurality of openings therein. Thus, dies for practicing the invention have a multiplicity of very small die openings or holes. All openings for any one die are preferably of equal size (i.e. equal in area dimension). The openings may vary from 0.1 to 4 millimeter diameter for different dies. Square or multi-sided openings may be used, but ideally, the openings are circular to give a cylindrical shape to resulting extrusions. The die is preferably oriented in a horizontal plane for vertical passage of the extruded material through the die. Such vertical discharge helps to prevent the initial material through the die from fowling the die openings. A heated die plate, i.e. one heated to the temperature of the last extruder zone, is also preferred.

A particularly useful extruder is the Wenger TX-52 extruder, commercialized by Wenger Manufacturing, Inc. of Sabetha, Kans., provided with two rotatable, flighted material advancing screws (screw elements of 52-mm diameter) with a total of 5 barrel sections and terminated in a spacer plate die. The screws will typically be inter-meshing and co-rotating. The die plate typically will have six die inserts, typically arranged in a hexagonal design, with a number of holes of the desired diameter in each insert, typically from 25 to 100 holes, each hole typically having a diameter of 0.1 mm to 2 mm, preferably from 0.4 mm to 0.6 mm. The design of the Wenger TX line of extruders is described in U.S. Pat. No. 4,875,847, which is incorporated by reference herein. The extruder is designed to heat the contents thereof and to expose the contents to significant compaction and shear. The temperature of the contents of the extruder should be maintained sufficiently low such that the entire mass of tocopherol succinate is not melted. Thus, the temperature of the entire contents of the extruder should not be allowed to exceed a temperature of 72° C. Typically, the temperature of the mass will be below 70° C., more typically below 65° C. Typically, the tocopheryl succinate will be fed into the extruder at ambient temperature, and will be gradually heated to a temperature of 55° C. to 65° C., more typically to a temperature of 60° C. to 63° C., just prior to exit of the material from the extruder. With a five section extruder, the set temperature of the heating medium will typically be 45° C. to 55° C., in the first two sections (e.g. contents in these two sections typically at 30° C. to 35° C.), 50° C. to 60° C. in the third and fourth sections (e.g. contents in third section typically 52° C. to 56° C. and in the fourth section 55° C. to 60° C.) and 58° C. to 62° C. in the last section (e.g. contents in last section 60° C. to 62° C.). It may be desirable to expose portions of the plastic mass to, e.g. that portion of the mass in contact or close proximity with the interior wall of the barrel of the extruder or the die plate, to temperatures that are in excess of 72° C., e.g. 75° C., to provide lubrication of the wall or die plate. In such a case, however, one should ensure that the entire mass will not reach a temperature above 72° C. the melting temperature of tocopherol succinate. The maximum preferred temperature when using tocopheryl succinate and its mixtures with non-plastic supplements, is 125° C. The product will typically be fed to an extruder such as the Wenger TX-52 at a rate of 70 to 75 kg/hr and the screw speed will typically be between 160 rpm and 165 rpm.

The product of the extrusion will be a material which, upon cooling, sets to form a solid product within a matter minutes, typically less than 1 hour, more typically at most 30 minutes, and more preferably at most 10 minutes. Preferably, the mass sets to a solid form in a matter of a few seconds, typically from 1 second to 30 seconds. It has been found that the material which takes a relatively longer time to set (which typically results when the plastic mass is heated to a a relatively high temperature) appears to be harder after setting than the material which sets more quickly. The material which sets more quickly is thus, more fragile and friable than the material which takes a longer time to set. For materials which melt at temperatures of 40° C. it may be necessary to use cooling means to form a solid from the plastic material more quickly. Cooling means such as a cooled belt or cooled gases passing over the material can be used. Liquid nitrogen or carbon dioxide can be useful.

The extrudate will typically be in the form of a rope or plurality of ropes which can then be subjected to size reduction to obtain a product having the desired particle size. Size reduction is discussed in *Encyclopedia of Chemical Technology,* vol. 21, pp. 132–162 (John Wiley & Sons, Inc., N.Y., N.Y. 1983) the disclosure of which is incorporated herein by reference. The apparatus chosen for size reduction is preferably one which accomplishes size reduction by impact, and with minimal, if any, shear or compaction. Examples of preferred size reduction apparatus include a disk mill or pin mill. In such mills, the tocopheryl succinate will come into contact with striking members, e.g. bars or pins, attached perpendicularly to the plane of a rotating member, e.g. a disk or plate. The impact of the tocopheryl succinate will cause a reduction in the size of the particles thereof. There is preferably no surface in contact with or within close tolerance of the striking members so that there will be little of no shear or compaction, as opposed to free impact, applied to the particles. The chamber of such a mill is typically bounded with a screen with openings therein which will allow material of the desired size to exit the chamber therethrough. An example of a preferred impact mill is the model SM-18 Prema Mill, Prater Industries, Inc., Chicago, Ill. Such a grinder can typically produce 60 pounds/hr when operated at a tip speed of 10 meters/second.

In preferred embodiments, the extrudate will be in an elongated form, e.g. ropes, which have a diameter of roughly the size desired of the powdered particle, e.g. from 0.4 mm to 0.6 mm. Thus, the size reduction will serve largely to reduce the elongated dimension of the ropes to roughly the size of the diameter of the rope. Of course, the size reduction process will also serve to break the particles along the axial direction as well, so that the average diameter of the resulting product will be less than the diameter of the elongated starting material.

During size reduction, the tocopheryl succinate should be maintained below the melting point of the product, preferably at or below ambient temperature of 25° C. Cooling air or other cooling fluid, e.g. liquid nitrogen, can be introduced into the milling chamber to cool the product during size reduction.

In typical operation, the process will entail dropping tocopherol succinate powder into a feeder which in turn feeds the powder to an extruder at a controlled rate. The extruder heats the powder with shear and pressure to form a plastic mass of material that is not fully melted. The pressure generated by the extruder forces the plastic material through die openings at the end of the extruder barrel. Upon exiting the extruder, the extruded material is vertically discharged onto a belt. The belt conveys the extruded material for sufficient time for the material to harden to a solid form. The hardened material then falls off the end of the belt into coarse crushing wheels which break the strands of extrudate into shorter, but still elongated pieces. The size reduced material falls into a holding bin prior to passing to a feeder. The feeder then feeds the size reduced material to a grinder at a controlled rate. The grinder is cooled to prevent material from melting. The grinder reduces the particle size of the material to a desired range. The ground material is then screened to remove particles considered too large (e.g. those retained on a 14-mesh screen) and too small (those passed by a 120-mesh screen). The material which is too small can be added to the feed of the extruder and the material which is too large can be added to the feed of the grinder.

The product can be characterized as a powdered composition. If desired, it can be sieved in order to obtain a desired grain size distribution. An excessively fine composition is undesirable because of its poor flowability in charging into dies in tabletting. An excessively coarse composition is unsuited for admixture with some other composition and moreover causes weight fluctuation in tablet manufacture. A typical lower limit on grain size is typically a maximum of 5% by weight of the grains through a 120-mesh sieve. Typically, the product will have less than 5% retained on a 14-mesh sieve. Preferably at least 85% of the material will pass a 25-mesh sieve, but will be retained on a 60-mesh sieve.

The mesh sizes as defined in this specification are those specified in the relevant U.S. standard (as published in *Handbook of Chemistry and Physics*, p. F-158 (57 the ed., CRC Press, Cleveland Ohio, 1976)). Said mesh sizes and the corresponding sieve opening sizes are shown below.

| Mesh | Sieve opening size (micrometers) |
| --- | --- |
| 10 | 2,000 |
| 20 | 850 |
| 80 | 180 |
| 120 | 125 |

In another embodiment of the invention the tocopheryl succinate or the phytosterol plastic nutritional supplements may be atomized. Extrusion involves turning the tocopheryl succinate or the phytosterol into a fluid mass without fully melting it, atomizing it into spherical particles and allowing the particles to harden into a free flowing powder.

In extrusion the heating and shear in the extruder forms a plastic mass of material. The viscosity of the plastic material can be controlled in the extruder to allow it to be more fluid (less viscous). The plastic, flowable mass can be extruded directly into a spray nozzle with sufficient viscosity to allow it to be atomized. The nozzle atomizes the material into droplets. These droplets are allowed to fall for a time sufficient to allow them to harden and loose their plasticity. The hard particles are collected as a free flowing powder.

The spray nozzle of choice in this case is a two fluid or three fluid spray nozzle. In a two fluid nozzle the one fluid is the plastic, flowable material and the second fluid is air or steam for external atomization. In the three fluid nozzle air or steam is mixed inside the nozzle with the plastic, flowable material and the third fluid is air or steam for external atomization. An inert gas like nitrogen or a fluid like liquid nitrogen may also be used. A centrifugal wheel atomizer may also be used.

This process is similar to prilling but the material being prilled is not fully melted.

A desirable attribute of this process is that it forms a more spherical particle which has better flow properties than cylindrical particles and it eliminates the necessity of a grinding step.

Details of industrial atomization of this type may be found in U.S. Pat. No. 5,549,917 to Cherukuri et al., incorporated herein in its entirety as if it set forth in full.

The tocopheryl succinate and phytosterols according to the invention can be used as raw materials in the manufacture of tocopheryl succinate and phytosterol-containing tablets and capsules. Tabletting of the powder is carried out by a conventional method in the presence of a lubricant and, if necessary, some other drug substance and/or an excipient (e.g. lactose, sucrose, mannitol). As said lubricant, there may be mentioned those lubricants which are used in conventional tablet manufacture, such as stearic acid and stearates (e.g. magnesium stearate, calcium stearate) and talc. The amount and kind of the lubricant are selected within such a range as to give tablets which are practical from the strength and disintegration viewpoint. Typically, it is used in an amount of 0.1 to 7 percent by weight based on the main active substance. Of the lubricants, a stearate or stearic acid is typically added in an amount of at least 0.5 percent by weight based on the main active substance. The above-mentioned other drug substance can include a variety of vitamins, mineral, and other dietary supplements. The compression is normally carried out under the condition of 1 to 2 ton/cm$^2$.

The following examples will illustrate the invention and should not be construed to limit the invention, except as expressly noted in the appended claims. All parts, ratios and percentages stated herein are by weight unless noted otherwise in context.

EXAMPLES

Example 1

Tocopheryl succinate powder (available from Henkel Corp., Ambler, Pa., as Covitol 1210) is charged to a Wenger TX-52 extruder. The extruder had five barrel sections, the set temperature and actual temperature of the contents of each section being set forth below. The die consisted of a die plate with six inserts each having 61 openings, each opening 0.5 mm in diameter. A 90° elbow was attached to the end of the extruder. A six insert die plate was attached to the end of the elbow. Throughout the trial Covitol 1210 (TM Henkel Corp., LaGrange Ill.) was used as the feed for the extruder. The extruded material was discharged vertically downward. The 0.5 mm die inserts were the only inserts used during the trial. The running conditions of the trial are listed in the following Table 1.

TABLE 1

| Run | 1 | 2 | 3 |
| --- | --- | --- | --- |
| Feed Screw Spd. (rpm) | 20 | — | — |
| Extruder Shaft Speed (rpm) | 100 | 162 | 175 |
| Extr. Motor. Load (%) | 24 | 31 | 30 |
| Zone #1 Set/Act. (° C.) | 50/38 | 50/32 | 50/32 |
| Zone #2 Set/Act. (° C.) | 50/38 | 50/32 | 50/32 |
| Zone #3 Set/Act. (° C.) | 55/57 | 55/56 | 55/56 |
| Zone #4 Set/Act. (° C.) | 60/60 | 60/60 | 60/60 |
| Zone #5 Set/Act. (° C.) | 60/60 | 60/61 | 60/61 |

TABLE 1-continued

| Run | 1 | 2 | 3 |
|---|---|---|---|
| Die Config. & Dia. | 6 × 61 × 0.5 mm | 6 × 61 × 0.5 mm | 6 × 61 × 0.5 mm |
| Total Die Opening (cm$^2$) | 2.875 | 2.875 | 2.875 |
| Zone #4 Press. (kpa) | 0 | 4830 | 4830 |
| Zone #5 Press. (kPa) | 5170 | 6210 | 6210 |
| Rate (kg/hr.) | 36 | 72 | 78 |

The product of run 2 of the above extrusion was then ground in a Prema SM-18 impact mill, Prater Industries, Chicago, Ill. For each run the material was loaded into a bin and fed into the grinder using a vibrating feeder. The screen surrounding the impeller had holes of approximately 2.4 mm. (This size is larger than the particles which pass through the screen because the angle at which the particles typically approach the screen causes the apparent diameter of the holes to be smaller than 2.4 mm.) The running conditions and screening results of each trial are listed in Table 2.

TABLE 2

| Run # | 1 | 2 | 3 |
|---|---|---|---|
| Rotor Tip Speed (m/s) | 10 | 16 | 27 |
| No Load/Run Load (amps) | 0.61/0.8 | 0.6/1.0 | 1.0/2.3 |
| Feed Rate (lbs/hr) | 60 | 112 | 112 |
| % on 14 Mesh Screen | — | — | — |
| % on 25 Mesh Screen | 5.4 | 2.1 | 0.4 |
| % on 30 Mesh Screen | 31.8 | 13.2 | 7.2 |
| % on 40 Mesh Screen | 53.3 | 43.8 | 50.8 |
| % on 60 Mesh Screen | 8.4 | 38.5 | 33.3 |
| % on 120 Mesh Screen | 0.2 | 0.9 | 3.0 |
| % on 140 Mesh Screen | — | 0.3 | 1.4 |
| % Less Than 140 Mesh Screen | 0.2 | 1.2 | 3.5 |

The process has been described in relation to forming particulate tocopherol succinate (vitamin E succinate). The method can be applied to other plastic nutrient supplement compositions.

Example 2

As in Example 1, however the extrudate was blasted with liquid nitrogen as it left the extruder to atomize the extrudate into particulates.

Example 3

The extruder of Example 1 is fitted with an injection molding head in order to mold tablets directly.

Example 4

A blend of sterols as described above (comprising beta-sitosterol, campesterol, stigmasterol and brassicasterol) and available as Generol 122 (TM Henkel Corp., LaGrange, Ill.) is extruded in a manner similar to Example 1.

Example 5

A blend of sterols as described above (comprising beta-sitosterol, campesterol, stigmasterol and brassicasterol) and available as Generol 100 (TM Henkel Corp., LaGrange, Ill.) is extruded in a manner similar to Example 1.

Example 6

The extruder of Example 1 is fitted with an atomizing nozzle that atomizes the extrudate to form a free flowing powder.

The present invention requires that the material to be treated, whether it is a single nutritional supplement or a mixture of nutrition supplements to a temperature at which the mixture is a plastic mass but not molten and cooling the material to a solid form. The solidified material can be comminuted to form particles within a prescribed size range.

It is critical that the entire composition not be melted. Melting the entire composition makes the material difficult to cool and solidify. The composition is heated and mixed at a temperature at which the mixture is plastic mass but not completely melted. It is not known whether the composition becomes plastic without any portion of the composition being melted or a portion of the composition becomes molten and causes agglomeration and plastification of the composition. Both effects may occur depending on the composition.

If the composition is an unseparated mixture of several different materials, the composition may exhibit a broad softening range rather than a sharp melting point. These compositions are preferably heated to a temperature at the low end of the softening range so that the composition can be cooled and solidified more rapidly.

If the composition is a mixture of particles of different compositions, it can be processed directly by the process of the invention or the mixture can be homogenized by known methods before being treated by the process of the invention. Homogenization is particularly useful when one of the materials in the composition is a liquid at room temperature.

What is claimed is:

1. A process for producing a substantially physiologically inert binder free, particulate composition wherein the binder consists essentially of a plastic nutritional supplement which process comprises:

heating a mass of the plastic nutritional supplement to a temperature not above about 170° C., effective to form a plastic but not completely molten, mass of material, extruding the plastic mass of material into at least one elongated form;

cooling the elongated form for a sufficient Time for the elongated form to set to a solid form; and comminuting the solid form.

2. A process of producing a substantially binder free particulate composition comprising a plastic nutritional supplement which comprises:

heating a mass of the plastic nutritional supplement to an elevated temperature effective to form a plastic, but not completely molten, mass of material;

extruding the plastic mass of material into an atomizer head; and atomizing the plastic mass of material into particles.

3. The process of claim 1 wherein the heating is accomplished in an extrusion zone.

4. The process of claim 1 wherein the elongated form is a rope having a diameter of from about 0.1 mm to about 2 mm.

5. The process of claim 4 wherein the diameter is from about 0.4 mm to about 0.6 mm.

6. The process of claim 1 wherein the elongated form sets to a solid form within one hour of the beginning of the cooling of the elongated form.

7. The process of claim 1 wherein the elongated form sets to a solid form within about 30 minutes of the beginning of cooling the elongated form.

8. The process of claim 1 wherein the elongated form sets to a solid form within about 10 minutes of the beginning of cooling the elongated form.

9. The process of claim 1 wherein the elongated form sets to a solid form in less than about 30 seconds of the beginning of cooling the elongated form.

10. The process of claim 1 wherein the solid form is comminuted by impacting the solid form.

11. The process of claim 10 wherein the comminuting does not compact the particles.

12. The process of claim 1 wherein the solid form is comminuted in an impact zone where there is no contact of impacting members of the impact zone with an opposing surface of the impact zone.

13. The process of claim 1 wherein the comminuted product has a particle size distribution wherein not more than 5% by weight passes through a 120-mesh sieve.

14. The process of claim 1 wherein the comminuted product has a particle size distribution wherein less than 5% by weight is retained on a 14 mesh sieve.

15. The process of claim 1 wherein the comminuted product has a particle size distribution wherein at least about 25% by weight of the comminuted product passes through a 25 mesh sieve and is retained on a 60-mesh sieve.

16. The process of claim 1 wherein the plastic nutritional supplement is selected from the group consisting of tocopheryl succinate, phytosterols and mixtures thereof.

17. The process of claim 16 wherein the phytosterols are selected from the group consisting of sterols, sterol esters, stanols, stanol esters and mixtures thereof.

18. The process of claim 17 wherein the sterols are selected from the group consisting of alpha-sitosterol, beta-sitosterol, gamma-sitosterol, campesterol, stigmasterol, brassicasterol and mixtures thereof.

19. The process of claim 17 wherein the stanols are selected from the group consisting of stigmastanol, ergostanol, campestanol and mixtures thereof.

20. The process of claim 17 wherein the phytosterols comprise:

beta-sitosterol;

campesterol;

stigmasterol; and brassicasterol.

21. The process of claim 17 wherein the phytosterols comprise:

about 43 to about 53 wt. % beta-sitosterol;

about 22 to about 26 wt. % campesterol;

about 17 to about 19 wt. % stigmasterol; and about 2 wt. % brassicasterol, wherein wt % is based on the total plant extract.

22. The product of the process of claim 1, wherein said product comprises phytosterols.

23. A process of producing a substantially physiologically inert binder free, particulate composition wherein the binder consists essentially of a plastic nutritional supplement which comprises:

heating a mass of the plastic nutritional supplement to an elevated temperature effective to form a plastic, but not completely molten, mass of material;

extruding the plastic mass of material into an injection molding head; and molding tablets of said plastic nutritional supplement.

24. The process of claim 23 wherein the elevated temperature is not above about 170° C.

25. The process of claim 23 wherein the heating is accomplished in an extrusion zone.

26. The process of claim 23 wherein the plastic nutritional supplement is selected from the group consisting of tocopheryl succinate, phytosterols and mixtures thereof.

27. The process of claim 26 wherein the phytosterols are selected from the group consisting of sterols, sterol esters, stanols, stanol esters and mixtures thereof.

28. The process of claim 27 wherein the sterols are selected from the group consisting of alpha-sitosterol, beta-sitosterol, gamma-sitosterol, campesterol, stigmasterol, brassicasterol and mixtures thereof.

29. The process of claim 27 wherein the stanols are selected from the group consisting of stigmastanol, campestanol, ergostanol and mixtures thereof.

30. The process of claim 26 wherein the phytosterols comprise:

beta-sitosterol;

campesterol;

stigmasterol; and brassicasterol.

31. The process of claim 26 wherein the phytosterols comprise:

about 43 to about 53 wt. % beta-sitosterol;

about 22 to about 26 wt. % campesterol;

about 17 to about 19 wt. % stigmasterol; and about 2 wt. % brassicasterol, wherein wt. % is based on the total plant extract.

32. The tablets of the process of claim 23.

33. The particles of the process of claim 2, wherein said particles comprise phytosterols.

34. The process of claim 2 wherein the elevated temperature is not above about 170° C.

35. The process of claim 2 wherein the heating is accomplished in an extrusion zone.

36. The process of claim 2 wherein the plastic nutritional supplement is selected from the group consisting of tocopheryl succinate, phytosterols and mixtures thereof.

37. The process of claim 36 wherein the phytosterols are selected from the group consisting of sterols, sterol esters, stanols, stanol esters and mixtures thereof.

38. The process of claim 37 wherein the sterols are selected from the group consisting of alpha-sitosterol, beta-sitosterol, gamma-sitosterol, campesterol, stigmasterol, brassicasterol and mixtures thereof.

39. The process of claim 37 wherein the stanols are selected from the group consisting of stigmastanol, ergostanol, campesterol and mixtures thereof.

40. The process of claim 37 wherein the phytosterols comprise:

beta-sitosterol;

campesterol;

stigmasterol; and brassicasterol.

41. The process of claim 37 wherein the phytosterols comprise:

about 43 to about 53 wt. % beta-sitosterol;

about 22 to about 26 wt. % campesterol;

about 17 to about 19 wt. % stigmasterol; and about 2 wt. % brassicasterol, wherein the wt. % is based on the total plant extract.

* * * * *